United States Patent
Kilger et al.

(10) Patent No.: US 6,225,092 B1
(45) Date of Patent: May 1, 2001

(54) METHOD FOR THE UNCOUPLED, DIRECT, EXPONENTIAL AMPLIFICATION AND SEQUENCE OF DNA MOLECULES WITH THE ADDITION OF A SECOND THERMOSTABLE DNA POLYMERASE AND ITS APPLICATION

(75) Inventors: Christian Kilger; Svante Pääbo, both of München (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/991,184

(22) Filed: Dec. 16, 1997

(30) Foreign Application Priority Data

Dec. 20, 1996 (DE) .............................. 196 53 494

(51) Int. Cl.⁷ ...................................... C12P 19/34
(52) U.S. Cl. .................. 435/91.2; 435/91.1; 435/810
(58) Field of Search ................... 435/91.2, 810, 435/91.1

(56) References Cited

U.S. PATENT DOCUMENTS

| | | | |
|---|---|---|---|
| 4,962,020 | 10/1990 | Tabor et al. ............................. | 435/6 |
| 5,409,811 | 4/1995 | Tabor et al. ............................. | 435/6 |
| 5,427,911 | 6/1995 | Ruano ..................................... | 435/6 |
| 5,432,065 * | 7/1995 | Fuller .................................. | 435/91.1 |
| 5,512,462 | 4/1996 | Cheng ................................. | 435/91.2 |
| 5,556,772 | 9/1996 | Sorge et al. ........................ | 435/91.2 |
| 5,614,365 * | 3/1997 | Tabor et al. ............................ | 435/6 |
| 5,789,168 * | 8/1998 | Leushner et al. ........................ | 435/6 |
| 5,830,657 * | 11/1998 | Leushner et al. ........................ | 435/6 |
| 5,928,906 * | 7/1999 | Koster et al. ........................ | 435/91.2 |

FOREIGN PATENT DOCUMENTS

| | | |
|---|---|---|
| 0 727 496 | 8/1996 | (EP) . |
| 94/26766 | 11/1994 | (WO) . |
| 96/10640 | 4/1996 | (WO) . |
| 96/41014 | 12/1996 | (WO) . |

OTHER PUBLICATIONS

Chemical Abstracts, vol. 125, No. 25, 1996, p. 393, 125:319052.

Tabor et al., Proc. Natl. Acad. Sci. USA, vol. 92, pp 6339–6343, Jul. 1995, "A single residue in DNA polymerases of the *Escherichia coli* DNA polymerase I family is critical for distinguishing between deoxy–and dideoxyribonucleotides".

Kliger et al., Nucleic Acids Research, vol. 25, No. 10, May 1997, pp. 2032–2034 "Direct DNA sequence determination from total genomic DNA".

International Publication No. WO 93/02212, published Feb. 4, 1993.

Hwang et al., Analytical Biochemistry, vol. 231, No. 2, Nov. 1995, pp. 460–463, "Direct automated sequencing of singl lambda–phage plaques by exponential amplification sequencing".

Sarkar et al., Nucleic Acids Research, 1995, vol. 23, No. 7, pp 1269–1270, "Semi Exponential cycle sequencing".

Kilger et al., Biol. Chem., vol. 378, pp 99–105, Feb. 1997, "Direct exponential Amplification and Sequencing (DEXAS) of Genomic DNA".

International Publication No. WO 97/42348, published Nov. 13, 1997.

International Publication No. WO 97/40939, published Nov. 6, 1997.

International Publication No. WO 97/23650, published Jul. 3, 1997.

International Publication No. WO 97/41257, published Nov. 6, 1997.

International Publication No. WO 97/41258, published Nov. 6, 1997.

International Publication No. WO 97/41259, publishied Nov. 6, 1997.

Deng et al., Journal of Microbilogical Methods, vol. 17 (1993) 103–113, "Simultaneous amplification and sequencing of genomic DNA (SAS) . . . . ".

Rao, Analytical Biochemistry, vol. 216, 1–14 (1994), "Direct Sequencing of Polymerase Chain Reaction–Amplified DNA".

* cited by examiner

Primary Examiner—Kenneth R. Horlick
(74) Attorney, Agent, or Firm—Arent Fox Kintner Plotkin & Kahn, PLLC

(57) ABSTRACT

Method for sequencing a nucleic acid molecule in a thermocycling reaction which initially comprises a nucleic acid molecule, a first primer, a second primer, a reaction buffer, a first thermostable DNA polymerase, (optionally) a thermostable pyrophosphatase, deoxynucleotides or derivatives thereof and a dideoxynucleotide or a derivative thereof and which is characterized in that the thermocycling reaction additionally contains a second thermostable DNA polymerase which, in comparison to the said first thermostable DNA polymerase, has a reduced ability to incorporate dideoxynucleotides as well as the use of the said method.

62 Claims, 7 Drawing Sheets

A

B

GAAGCAGAGTTTTTAGGATTCCCGAGTAGCAGATGACCATGACAAGCAGC
300       310        320       330       340

C

GAAGCAGAGTTTTTAGGATTCCCGAGTAGCAGATGACCATGACAAGCAG
300       310        320       330       340

D

GAAGCAGAGTTTTTAGGATTCCCGAGTCGCAGA TGACCATGACAAGCAG
  310       320       330        340       350

E

C R AAGCAGA KTTTTTAGGATT CCMGA G
       300              310

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(xi) SEQUENCE DESCRIPTION: SEQ ID NO: 1:

GGCTGGTCCT GCCGCTGCTT GTCAT      25

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(xi) SEQUENCE DESCRIPTION: SEQ ID NO: 2:

CTGCTCCCCA GTGGATCGGG TGTAAAC      27

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 3:

CACCTTTGGG GTGGTGACAA GTGTGAT          27

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 4:

CGACGTTGTA AAACGACGGC CAGT          24

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 5:

CAGGAAACAG CTATGAC          17

METHOD FOR THE UNCOUPLED, DIRECT, EXPONENTIAL AMPLIFICATION AND SEQUENCE OF DNA MOLECULES WITH THE ADDITION OF A SECOND THERMOSTABLE DNA POLYMERASE AND ITS APPLICATION

The present invention relates to a method for the uncoupled, direct, exponential amplification and sequencing of DNA molecules by the addition of a second thermostable DNA polymerase and it also relates to the application of the said method. The uncoupled, direct, exponential amplification and sequencing of DNA molecules by the addition of a second thermostable DNA polymerase is referred to as "DEXTAQ" in the following.

TECHNICAL FUNDAMENTALS

The DNA sequence determination as developed by Sanger et al. ((1977) *Proc. Natl. Acad Sci. USA* 74, 5463–5467) is usually carried out with a T7 DNA polymerase (Tabor S. and Richardson, C. C. (1989) *Proc. Natl. Acad Sci. USA* 86, 4076–4080). This method requires relatively large amounts of a purified, single-stranded DNA template. Recently cycle sequencing has been developed (Murray, V. (1989) *Nucleic Acids Res.* 17, 8889). This method does not require a single-stranded template and allows the sequence reaction to be initiated with relatively small amounts of template. However, the template DNA has to be purified to almost complete homogeneity and is usually prepared by means of cloning in plasmids (Bolivar, F. et al., (1977) *Gene* 2, 95–113) and subsequent plasmid purification (Birnboim, H. C. and Doly, J. (1979) *Nucleic Acids Res.* 7, 1513–1523) or by means of PCR amplification (Mullis, K. B. and Faloona, F. A. (1987) *Methods Enzymol.* 155, 335–350). Only one primer is used in both of the methods described above.

Known thermostable polymerases that are used for cycle sequencing e.g. ThermoSequenase and Taquenase carry a mutation which is known as the "Tabor Richardson" mutation (Tabor, S. & Richardson, C. C. (1995) *Proc. Natl. Acad. Sci. USA* 92, 6339–6343) in which a tyrosine is present instead of a phenylalanine in the crevice of the enzyme which, during polymerization of the DNA molecule being formed, is responsible for discriminating between the incorporation of either deoxynucleotides or dideoxynucleotides. Such enzymes or functional derivatives thereof have an increased ability to incorporate dideoxynucleotides into DNA fragments that are being formed and can be used to improve the signal uniformity in sequencing reactions. The increased ability of the aforementioned DNA polymerases with a Tabor-Richardson mutation to incorporate dideoxynucleotides increases the statistical probability that a chain termination occurs due to incorporation of a dideoxynucleotide into a DNA molecule being formed.

In one embodiment of the cycle sequencing which is referred to as "coupled amplification and sequencing" or "CAS" Ruano and Kidd ((1991) *Proc. Natl. Acad Sci. USA* 88, 2815–2819; U.S. Pat. No. 5,427,911) have shown that one can use a two-step protocol to generate sequences from DNA templates. In the first step 15 PCR cycles are carried out with Taq DNA polymerase in the absence of dideoxynucleotides in order to prepare an adequate amount of sequencing template. In a second step in which dideoxynucleotides and a labelled primer are added, CAS produces the sequence as well as the additional amplification of the target sequence. Two primers are used in both steps of the method.

Taq DNA polymerase, that is used in coupled DNA sequencing reactions strongly discriminates against ddNTPs and preferably incorporates dNTPs if it is furnished with a mixture of ddNTPs as well as dNTPs. In addition, it incorporates each ddNTP, i.e. ddATP, ddGTP, ddCTP, ddTTP, with a strongly varying efficiency. Hence the optimization of the CAS process requires careful titration of the dideoxynucleotides.

Furthermore since coupled amplification and sequencing depends on the amount of the initial DNA, the distance between the two primers and the concentrations and the ratios of the ddNTPs and dNTPs relative to one another and to each other, the optimization of coupled amplification and sequencing reactions (CAS) requires that the reaction conditions are individually optimized for a particular DNA fragment.

All methods described above require a separate step for template production, CAS accomplishes this with an interruption between the first step for the exponential amplification of the template DNA and the second step for the synthesis of truncated DNA molecules. Also, all methods require the individual optimization of a given DNA fragment which can be tedious and time-consuming and can lead to errors especially when sequencing a large number of different DNA molecules or when processing large amounts of samples in a hospital or laboratory or when sequencing rare samples for forensic or archaeological studies.

For this reason it would be advantageous to have available a method for sequencing nucleic acids which simultaneously potentiates the exponential amplification of molecules of full length and of molecules of truncated length in the reaction which leads to a reduction of the required amount of starting nucleic acid molecules and does not require an interruption of the exponential amplification step and of the sequencing step so that the whole reaction can be carried out more rapidly and with fewer manipulations.

Furthermore it would also be advantageous to have available a method for sequencing nucleic acid molecules which allows an increase in the distance between the positions of the two primers on the nucleic acid molecule to be sequenced, is relatively independent of the distance between the said primers and in general does not require an optimization of the reaction conditions for each DNA fragment to be sequenced.

SUMMARY OF THE INVENTION

An object of the present invention is to provide an improved, rapid and reliable method for sequencing nucleic acid molecules.

A further object of the present invention is to provide a method for sequencing nucleic acid molecules that can be carried out in an uninterrupted manner, in a single step and in a single container.

A further object of the present invention is to provide a nucleic acid sequencing which simultaneously increases the exponential amplification of molecules of full length as well as of molecules of truncated length which leads to a reduction of the initial amount of nucleic acid molecules that are required for the cycling reaction.

A further object of the present invention is to provide a method for sequencing nucleic acid molecules which leads to an increase in the distance at which both primers can be positioned on the nucleic acid molecule to be sequenced.

A further object of the present invention is to provide a method for sequencing a nucleic acid which increases the signal-to-noise ratio of specific, correctly terminated molecules to unspecifically terminated molecules.

A further object of the present invention is to provide an application of the method according to the invention for sequence determination in medical diagnostics, forensics and population genetics.

Further objects of the invention can be deduced by a person skilled in the art from the description.

The thermocycling reaction of the present invention comprises a first primer and a second primer which serve to simultaneously produce sufficient template molecules of full length as well as molecules of truncated length which contribute to the sequencing of the nucleic acid molecule. Either one primer is labelled and the other is not or both are differently labelled. In addition each reaction initially contains the nucleic acid template to be sequenced as well as a buffer solution and the four deoxynucleotides or derivatives thereof and one dideoxynucleotide or another terminating nucleotide e.g. 3'-aminonucleotides or 3'-ester-derivatized nucleotides. A thermostable pyrophosphatase can be optionally added. Four reaction mixtures are prepared one for the determination of each base.

However, in contrast to the methods known in the state of the art, it was surprisingly found that direct, exponential amplification and sequencing can be carried out by adding two different types of DNA polymerases to the initial cycle sequencing reaction: a first thermostable DNA polymerase and a second thermostable DNA polymerase with a reduced ability to incorporate dideoxynucleotides compared to the said first thermostable DNA polymerase. The first DNA polymerase mainly produces truncated products that accumulate exponentially during the cycles and contribute to the sequence ladder that is generated whereas the second DNA polymerase, which has a reduced ability to incorporate dideoxynucleotides compared to the first said thermostable DNA polymerase, primarily produces products of full length which accumulate exponentially and serve in subsequent cycles as a template for the production of further DNA strands of full length as well as templates for extensions which contribute to the sequencing reaction. Hence the combination of the different properties of the two polymerases, i.e. the ability of the first DNA polymerase to efficiently incorporate dideoxynucleotides and the ability of the second DNA polymerase to efficiently incorporate deoxynucleotides, leads to a considerably increased efficiency of the uncoupled, direct, exponential amplification and sequencing reaction.

Therefore the present invention provides a method for nucleic acid sequencing (DEXTAQ) which simultaneously enables the exponential amplification of molecules of full length as well as of truncated length in a thermocycling reaction and leads to a reduction of the amount of initial nucleic acid molecules that are necessary for the reaction. This enables the sequencing of single-copy DNA fragments in amounts as small as ca. 60 ng genomic DNA.

Since, in addition, all reagents that are necessary for the exponential amplification of fragments of full length as well as of truncated fragments are present in the initial reaction mixture, the method of the present invention (DEXTAQ) achieves the simultaneous, exponential production of a sequencing template and of a sequence ladder in a single tube without the necessity of interrupting the thermocycling reaction. This means that using the method of the present invention it is possible to determine the nucleic acid sequence in a single step.

Furthermore the method of the present invention (DEXTAQ) allows the distance at which the two primers can be positioned on the template nucleic acid molecule to be enlarged. Thus the method according to the invention for example enables the 3'-ends of the first and of the second primer to be positioned on the DNA template at a distance that is larger than or equal to 500 bases.

Hence the aforementioned object of the present invention is achieved by providing a method for sequencing nucleic acid molecules in a thermocycling reaction which initially contains a nucleic acid molecule, a first primer, a second primer, a reaction buffer, a first thermostable DNA polymerase, deoxynucleotides or derivatives thereof, and a dideoxynucleotide or another terminating nucleotide and is characterized in that the thermocycling reaction additionally contains a second thermostable DNA polymerase which, in comparison to the said first thermostable DNA polymerase, has a reduced ability to incorporate dideoxynucleotides.

A single enzyme would also be suitable for use in the method according to the invention that has different enzyme activities e.g. by using a chimeric polymerase or by the fact that a fraction of the polymerase has a modified ability to incorporate dideoxynucleotides by the continuous or partial action of agents. If this enzyme is composed of several subunits then these subunits can be covalently or non-covalently linked together.

The present invention also enables three or more DNA polymerases to be used in this method.

In a preferred embodiment the method according to the invention is furthermore characterized in that each thermocycling reaction for the determination of the position of A, G, C and T in the said DNA molecule is carried out in a single step, in a single container, vessel or tube.

The use of a DNA polymerase is preferred as the thermostable first DNA polymerase which, in contrast to wild-type Taq DNA polymerase, has a reduced discrimination against ddNTPs in the buffer and under the conditions that are used for the thermocycling. More preferably a DNA polymerase is used which carries a "Tabor-Richardson" mutation or a functional derivative thereof which also has no 5'-3' exonuclease activity such as e.g. AmplitaqFS™ (Taq DNA polymerase (-exo5'-3') (F667Y), Tabor and Richardson (1995), loc. cit.), Taquenase™ (Taq DNA polymerase Δ235 (-exo5'-3') (F667Y), Tabor and Richardson (1995), loc. cit.) and ThermoSequenase™ (Taq DNA polymerase Δ272 (-exo5'-3') (F667Y), Tabor and Richardson (1995), loc. cit.) as well as mixtures thereof or other DNA polymerases and mixtures thereof which are thermostable can also be used in the method of the present invention. The use of Thermosequenase or some other DNA polymerase which has a better ability to incorporate ddNTPs is particularly preferred for the method of the present invention.

A DNA polymerase which carries no "Tabor-Richardson" mutation such as e.g. Taq DNA polymerase, Tth DNA polymerase, Klentaq (Taq DNA polymerase) (-exo5'-3'), (Korolev et al. (1995) Proc. Natl. Acad. Sci. USA 92, 9246–9268, W. Barnes in Proc. Natl., Acad. Sci. USA 91 (1994), 2216–2220 and U.S. Pat. No. 5,436,149 is preferably used as the thermostable second DNA polymerase which has a reduced ability to incorporate dideoxynucleotides compared to the first thermostable DNA polymerase. The use of Taq DNA polymerase in the method of the present invention is particularly preferred.

Processive polymerases are preferably used for the method according to the invention i.e. the polymerase with a reduced discrimination against ddNTPs preferably has a higher processivity than ThermoSequenase and the polymerase which discriminates against ddNTPs preferably has a higher processivity than the wild-type Taq DNA polymerase. Polymerases according to the invention are most preferably used for the present method whose processivity is higher than that of the wild-type Taq DNA polymerase. Hence it would for example be advantageous to use two polymerases whose processivity is the same as that of T7 polymerase.

The method according to the invention can also be carried out as a "hot start" method. This ensures that the activity of the polymerase or polymerases only starts at an increased temperature in order to suppress a polymerization on unspecifically hybridized primers at lower temperatures. One possibility is that the thermocycling reaction additionally contains a polymerase-inhibiting agent. Polymerase antibodies are for example commercially available which only denature at higher temperatures and thus release enzyme activity of the polymerase. However, polymerases modified by genetic engineering that are present in an inactive form at lower temperatures would also be conceivable.

In a further preferred embodiment of the method of the invention the ratio of the said primers is preferably higher than 1:1, more preferably between about 2:1 and about 3:1 and most preferably 2:1.

In a further preferred embodiment of the method of the invention the said primers have a length that can prevent annealing to unspecific DNA fragments by a high temperature during the cycling. This leads to a good signal-to-noise ratio. The said primers preferably have a length of at least 18 nucleotides.

Primers can be synthesized by means of methods known in the state of the art. For example primers can be synthesized using known methods which do not significantly change the stability or function of the said primers during the nucleic acid sequencing method of the present invention.

Furthermore PNA-DNA hybrid oligonucleotides (see Finn, P. J. et al., N.A.R. 24, 3357–3363 (1996), Koch, T. et al., Tetrahedron Letters, 36, 6933–6936 (1995), Stetsenko, D. A, et al., Tetrahedron Letters 37, 3571–3574 (1996), Bergmann, F. et al., Tetrahedron Letters 36, 6823–6826 (1995) and Will, D. W. et al., Tetrahedron 51, 12069–12082 (1995)) are also regarded as primers for the method according to the invention.

In a further preferred embodiment of the method of the invention the said first primer is labelled. Moreover it is preferable that the said first primer and second primer are labelled differently. Any agents or methods known in the state of the art can be used as single or differential labelling agents and methods, provided that the stability or function of the said primer in the DNA sequencing method of the present invention is not significantly changed. For example single and differential labels can be selected from the group which comprises those enzymes such as β-galactosidase, alkaline phosphatase, peroxidase and enzyme substrates, coenzymes, dyes, chromophores, fluorescent, chemiluminescent and bioluminescent labels such as FITC, Cy5, Cy5.5, Cy7, Texas-red and IRD40 (Chen et al., (1993), J. Chromatog. A 652: 355–360 and Kambara et al. (1992), Electrophoresis 13: 542–546) ligands or haptens such as e.g. biotin and radioactive isotopes such as $^3$H, $^{35}$S, $^{32}$P, $^{125}$I and $^{14}$C.

DEXTAQ is relatively insensitive to various buffers and various deoxynucleotides and dideoxynucleotide concentrations.

The number of thermocycles can be from about 18 to about 50 cycles depending on the amount of template DNA and its purity.

Buffer components which can be used can include Tris-HCl at a pH of about 9.0 to 9.5 and at a concentration of about 10 to 30 mM, ammonium sulfate at a concentration of about 10 to 20 mM preferably 15 mM, $MgCl_2$ at a concentration of about 3.5 to 5.5 mM, optionally about 0.05 mM mercaptoethanol, about 0.28% Tween20® and/or about 0.02% Nonidet 40® but, however, are not limited to these.

Deoxynucleotides may be selected from dGTP, dATP, dTTP and dCTP but are not limited to these. According to the invention it is additionally also possible to use derivatives of deoxynucleotides which are defined as those deoxynucleotides which are able to be incorporated by a thermostable DNA polymerase into growing DNA molecules that are synthesized in a thermocycling reaction. Such derivatives include thionucleotides, 7-deaza-2'-dGTP, 7-deaza-2'-dATP as well as deoxyinosine triphosphate that can also be used as a substitute deoxynucleotide for dATP, dGTP, dTTP or dCTP, but are not limited to these. The aforementioned deoxynucleotides and derivatives thereof are preferably used at a concentration of about 300 μM to 2 mM.

Dideoxynucleotides can be selected from ddGTP, ddATP, ddTTP and ddCTP but, however, are not limited to these. According to the invention it is also additionally possible to use derivatives of dideoxynucleotides which are defined as those dideoxynucleotides that are able to be incorporated by a thermostable DNA polymerase into growing DNA molecules that are synthesized in a thermo-cycling reaction. Preferred concentrations of ddNTPs are between about 1 and 5 μM.

The preferred ratio of dNTPs to ddNTPs (dNTPs:ddNTPs) that is used in the method according to the invention is between 100:1 and 1000:1 more preferably between 300:1 and 600:1.

In a further preferred embodiment of the method of the invention the said method is carried out at a temperature at which the signal-to-noise ratio of the specific, truncated DNA molecules compared to the unspecific DNA molecules is large enough not to substantially impede reading of the sequence. In the case of human single-copy DNA sequences the highest possible annealing temperature drastically reduces the background. For this the annealing and synthesis steps of the thermocycling reaction are carried out at a temperature of at least 55° C., preferably at 66° C. and most preferably at at least about 68° C.

In a further preferred embodiment of the method of the invention the nucleic acid molecule to be sequenced can be present as total genomic DNA which is in an uncloned or unpurified state. The genomic DNA can have a length of more than or equal to 2 kb. DEXTAQ functions with about 60 ng total genomic DNA, but also functions with smaller amounts of DNA if multicopy fragments are analysed. Other forms of DNA that can be used as templates include purified, partially purified or unpurified cloned DNA such as e.g. unpurified plasmid DNA from bacterial colonies or cloned or uncloned mitochondrial DNA etc. Furthermore the method of the present invention is relatively independent of the base composition of the template.

In a further preferred embodiment of the method of the invention the nucleic acid molecule to be sequenced can be present as RNA. A mixture of two polymerases is used: a first DNA polymerase according to the invention e.g. one which contains a "Tabor-Richardson" mutation or a functional derivative thereof, such as ThermoSequenase and a second DNA polymerase that is able to reversely transcribe RNA into DNA and has the ability to act as a PCR enzyme. Any thermostable DNA polymerase which has reverse transcriptase activity can be used as a second DNA polymerase for the method of the invention in which RNA is used as the template. Taq DNA polymerase (Jones et al., Nucl. Acids Res. 17:8387–8388 (1989)) or Tth DNA polymerase (Myers et al., Biochemistry 30:7666–7672 (1991)) is preferably used and more preferably Tth DNA polymerase. Tth polymerase reversely transcribes the RNA template into DNA which can then be used by both enzymes: Tth polymerase will primarily generate products of full length which can serve as templates and ThermoSequenase will produce truncated products (ddNTP incorporation) and thus a sequence ladder.

Suitable buffers include those that are described in Myers et al. (1991) Biochemistry 30: 7666–7672. The following buffer can be used for both polymerases and guarantees the function of both polymerases: 10 mM Tris-HCl (pH 8.3), 40 mM KCl, 1 mM $MnCl_2$. A reverse transcription using a reaction buffer and optionally $MgCl_2$ at a concentration of about 1 mM to 5 mM and which also includes both polymerases, both primers and nucleotides, is subjected to an incubation step (15 minutes at 70° C.). Afterwards the $MgCl_2$ concentration is adjusted to between 1 mM and 5 mM and a DEXTAQ reaction is carried out.

Suitable sources of nucleic acid molecules in the method according to the invention are body fluids such as sperm, urine, blood or fractions of these, hairs, an individual cell, cells or fractions thereof, hard tissue such as bones and soft tissue or fractions thereof and cell cultures or fractions thereof as well as bacteria, viruses or bacteriophages.

The present invention also provides an application of the method according to the invention for the determination of a nucleotide sequence of a given nucleic acid molecule e.g. for sequencing Shotgun libraries using two labels for large-scale genome projects and in medical diagnostics, forensics and population genetics. The method of the present invention can be used to detect genetic mutations or polymorphisms, to identify the origin of the sequenced nucleic acid or to detect the presence of foreign or infectious agents in a sample.

The present invention provides for the first time a method which enables the simultaneous amplification and sequencing of a nucleic acid fragment to be sequenced from a complex mixture of nucleic acids such as total genomic human DNA without prior amplification of the nucleic acid to be sequenced by means of known methods, in a single step i.e. without interrupting the reaction and indeed such that an unequivocal sequence ladder is readable.

A particular advantage of the method according to the invention is therefore the ability to directly sequence nucleic acids. Thus the method according to the invention can be used for the direct sequencing of e.g.

eukaryotic genomic DNA such as e.g. of human chromosomal DNA or mitochondrial DNA, human RNA unpurified plasmid DNA from bacterial colonies as well as unpurified single-stranded or double-stranded DNA from bacteriophages.

The present invention relates to all combinations of all procedures of the above methods.

After preparation the sequencing reactions can be applied directly to a sequencing gel such as e.g. after addition of a commonly used loading buffer (e.g. formamide which contains 20 mM EDTA (pH 7.4) and 6 mg/ml dextran blue) and denaturation (e.g. for 4 minutes at 96° C.). The sequence ladder can be read in correspondence with known methods.

The method of the invention is well suited for automation. Since the two primers in the reaction are provided with different labels which can for example be detected with two different wavelengths, the method of the present invention enables the simultaneous sequencing of both strands of a template and the detection of both reactions in one or several gel lanes. In general many DEXTAQ reactions using different dyes can be carried out simultaneously in the same tube and applied to a sequencing instrument that is equipped with several lasers or can be detected by other methods such as e.g. autoradiography.

Furthermore a kit for sequencing a nucleic acid molecule is also a subject matter of the present invention, wherein this kit contains a reaction buffer, deoxynucleotides or derivatives thereof and at least one dideoxynucleotide or a derivative thereof and at least one thermostable DNA polymerase with different abilities to incorporate dideoxynucleotides. A suitable first primer and the second primer are then added individually depending on the application and the nucleic acid molecule to be sequenced.

In order to sequence a nucleic acid molecule the kit contains, in a preferred embodiment, a first thermostable DNA polymerase and additionally a second thermostable DNA polymerase which, compared to the said first thermostable DNA polymerase, has a reduced ability to incorporate dideoxynucleotides.

Most preferably the kit for sequencing a nucleic acid molecule contains a first thermostable polymerase, Taq DNA polymerase (-exo5'-3') (F667Y) or a functional derivative thereof and a second thermostable DNA polymerase, Taq polymerase or a functional derivative thereof.

BRIEF DESCRIPTION OF THE DRAWINGS

FIG. 2F. 60 ng of total genoric DNA was subjected to an uncoupled, direct amplification and sequencing reaction using equimolar amounts i.e. 3 pmol each of an FITC-labelled primer (CCR5-2) and of an unlabelled primer (CCR5-1). The A.L.F. software was able to process 290 bases. The reactions were carried out using 0.25 units Taq DNA polymerase and standard ThermoSequenase reagents.

FIG. 3A shows a reaction in which 2.5 units Klentaq polymerase were added to a direct, uncoupled amplification and sequencing reaction which was carried out with 60 ng total genomic DNA. FIG. 3B shows a direct, uncoupled, exponential amplification and sequencing reaction which was carried out with standard Taq DNA polymerase and FIG. 3C shows a reaction in which 0.25 units Tth polymerase was added.

Figure 1:
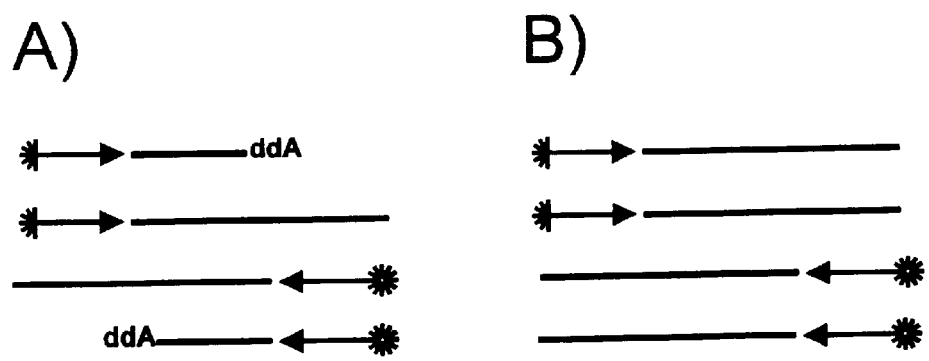
FIGS 1A and 1B. Schematic representation of the method of the present invention (DEXTAQ). A first polymerase of the present invention FIG. 1A which carries a "Tabor-Richardson" mutation for discriminating towards ddNTPs preferentially incorporates ddNTPs and produces the sequence ladder. A second polymerase of the present invention which, compared to the said first thermostable DNA polymerase FIG. 1B, has a reduced ability to incorporate dideoxynucleotides, preferably incorporates dNTPs and mainly produces products of full length and provides the uncoupled, direct, exponential amplification and sequence reaction with additional sequencing templates.

The invention is described more exactly and in more detail by the following non-limiting examples.

EXAMPLE 1

Template Preparation

Total genomic DNA was prepared from 2 ml blood samples using a rapid cleaning kit (Cambridge Molecular Technologies Ltd., Cambridge, UK). Purified DNA was diluted in ddH$_2$O to a concentration of 175 ng per µl.

Sequencing Reagents and Conditions

Unlabelled and FITC-labelled oligonucleotides were synthesized with an ABI DNA/RNA Synthesizer, Model 392. Cy5 labelled oligonucleotides were obtained from the Pharmacia Biotech Company (Freiburg, Germany). The following oligonucleotides were used:
SEQ ID NO. 1:
  (CCR5-1): 5'-GGC TGG TCC TGC CGC TGC TTG TCA T-3';
SEQ ID NO. 2:
  (CCR5-2): 5'-CTG CTC CCC AGT GGA TCG GGT GTA AAC-3';
SEQ ID NO. 3:
  (CCR5-3)5'-CAC CTT TGG GGT GGT GAC AAG TGT GAT-3' (Samson, M. et al., Biochemistry 35 (11), 3362–3367 (1996)),
SEQ ID NO. 4:
  (universal primer) 5'-CGA CGT TGT AAA ACG ACG GCC AGT-3' and
SEQ ID NO. 5:
  (reverse) 5'-CAG GAA ACA GCT ATG AC-3' (Pharmacia Biotech).

Direct, exponential amplification and sequencing reactions were carried out using Thermosequenase reagents (2).

A 24 µl mixture composed of 6 pmol of an FITC-labelled and 3 pmol of an unlabelled primer, 6 pmol of an FITC-labelled and 3 pmol of a Cy5-labelled primer, or 3 pmol of an FITC-labelled and 3 pmol of an unlabelled primer total genomic DNA (0.5 to 8 µl at a concentration of 120 ng/µl) and additional polymerase if necessary (0.1 to 2 µl depending on the unit definition) was prepared and 6 µl aliquots were added to 2 µl Thermosequenase termination mix. The sequencing reactions were carried out in a thermocycler with a heatable cover (MJ-Research, Watertown, Mass.). The reactions were stopped by adding 5 µl formamide (20 mg EDTA (pH 7.4) and 6 mg/ml dextran blue) which was followed by a 4 minute denaturation at 95° C. The sequencing reactions were analysed on an A.L.F. (Pharmacia Biotech, Uppsala, Sweden). HydroLink Long Rangersm (FMC, Rockland, Me.) gels and 30 cm glass plates were used in all cases. The gel conditions corresponded to the manufacturer's recommendations.

EXAMPLE 2

Two oligonucleotides with a length of 25 and 27 nucleotides which span 382 base pairs of the CCR5 gene were synthesized. One of the two oligonucleotides was labelled at the 5'-end with fluorescein (CCR5-2) whereas the other (CCR5-1) was unlabelled. Two reactions were prepared each containing 6 pmol of the labelled primer and 3 pmol of the unlabelled primer, 500 ng total genomic DNA and ThermoSequenase reagent which was composed of enzyme, reaction buffer and deoxy and dideoxy mixtures. 2.5 units of standard Taq polymerase was added to one of the two reactions. The reactions were incubated for 3 min. at 95° C. in order to enable a complete denaturation of the template DNA. Afterwards 45 cycles were carried out each consisting of 30 sec. at 68° C. and 40 sec. at 95° C. The reactions were stopped and denatured by the addition of formamide and heating to 95° C. for 4 minutes before they were applied to an A.L.F. sequencing apparatus.

If no additional Taq DNA polymerase had been added, the A.L.F. was able to process 344 bases. If, in contrast, 0.25 units Taq polymerase was added to the direct exponential amplification and sequencing reaction, 351 bases were determined. A visual analysis of the A.L.F. curves showed that the signal intensity improved where Taq DNA polymerase had been added. Furthermore the stops at the start of the run which can occur in direct exponential amplification and sequencing reactions were substantially reduced. In contrast the signal strength remained continuously high towards the amplifying primer. In contrast in the case in which no Taq DNA polymerase was present, the signal was weaker after 200 base pairs. The signal at the end of the run which corresponds to the product of full length was substantially stronger in the reaction in which Taq DNA polymerase was present.

EXAMPLE 3

In order to confirm the fact that additional Taq DNA polymerase is able to amplify the exponential factor and to reduce the background and also to determine the amount of Taq DNA polymerase required for an optimal reaction, a reduced amount of template DNA was used in combination with varying amounts of Taq DNA polymerase. Five reactions were prepared each containing 120 ng total genornic DNA, 6 pmol of the labelled primer and 3 pmol of unlabelled primer and ThermoSequenase reagent. In one reaction no additional Taq DNA polymerase was added. In the other 4 reactions 0.25, 0.5, 1.0 and 2.0 units Taq polymerase was added respectively. In order to exclude a possible effect of the Taq polymerase storage buffer, the storage buffer was added to that reaction to which no polymerase had been added. The reactions were subjected to the cycles described above.

In the case where no Taq DNA polymerase had been added the A.L.F. Manager was only able to process a few bases and the signal intensities were too low to be considered useful for routine sequencing. In the reactions in which 0.25 units and 0.5 units had been added the A.L.F. Manager was able to process 374 bases and 364 bases respectively. 226 bases were determined by the A.L.F. Manager in the reaction in which one unit Taq polymerase had been added.

Figure 2:
FIGS. 2A–2F. 60 ng of total genomic DNA was subjected to a direct, uncoupled sequencing reaction using 6 pmol of an FITC-labelled primer (CCR5-2) and 3 pmol of an unlabelled primer (CCR5-1). The section shown in all windows is only at a distance of 20 base pairs from the end of the template and the last bases are part of the primer that generates the second template. No additional Taq DNA polymerase was added to the reaction that is shown in FIG. 1A. Increasing amounts of Taq DNA polymerase were added to the reactions that are shown in FIG. 2B (0.25 units), FIG. 2C (0.5 units), FIG. 2D (1.0 units) and FIG. 2E (2.0 units). In cases where no Taq DNA polymerase had been added, the A.L.F. software was not able to process a sequence. A better ratio between signal and noise is seen in the cases in which Taq DNA polymerase had been added.
Figure 2:
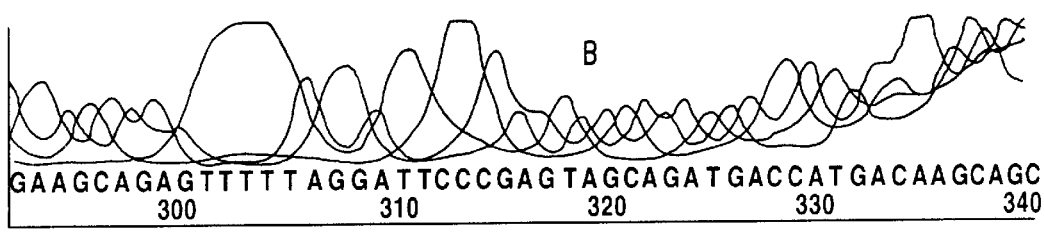
Figure 2:
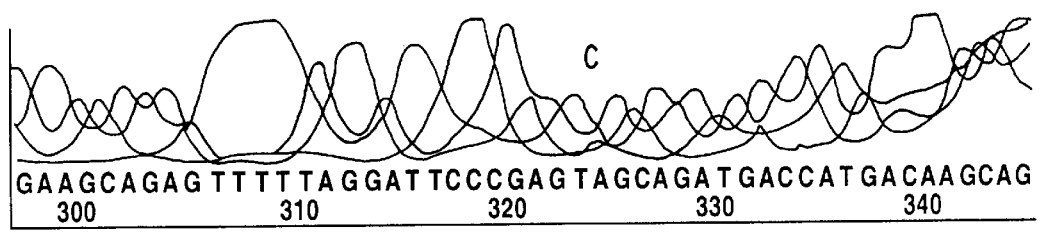
Figure 2:
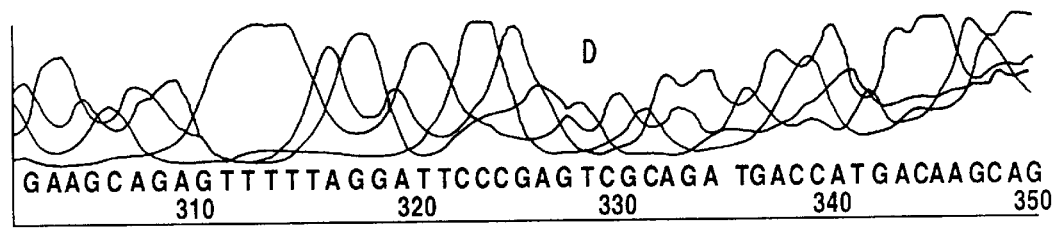
Figure 2:
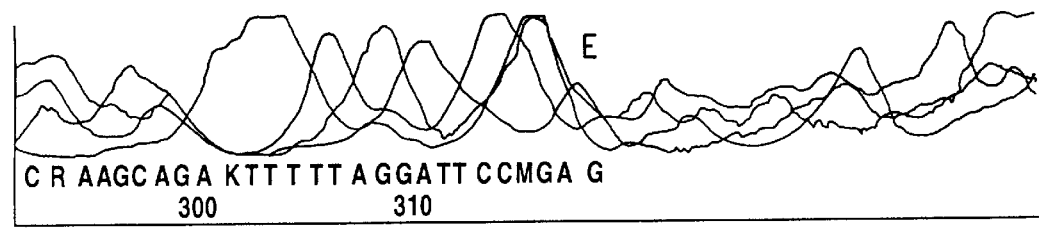
Figure 2F:
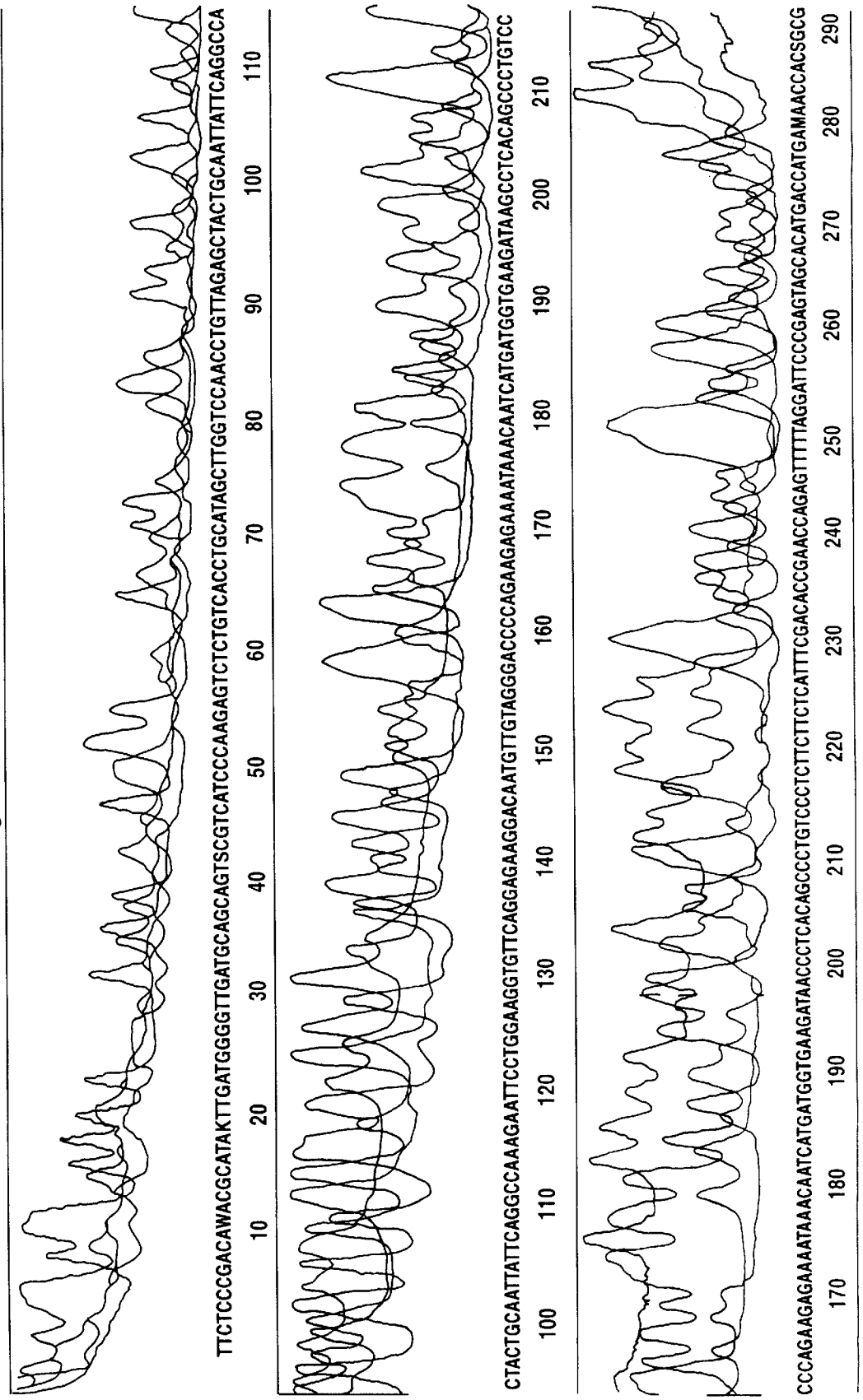

The reactions were repeated under identical conditions but using an even smaller amount of genomic DNA. 60 ng template DNA was sequenced using varying amounts of Taq DNA polymerase. No signal was detectable where no Taq polymerase had been added but the A.L.F. Manager was again able to process the sequence in cases where between 0.1 and 0.4 units Taq DNA polymerase had been added (FIG. 2).

EXAMPLE 4

Figure 3:
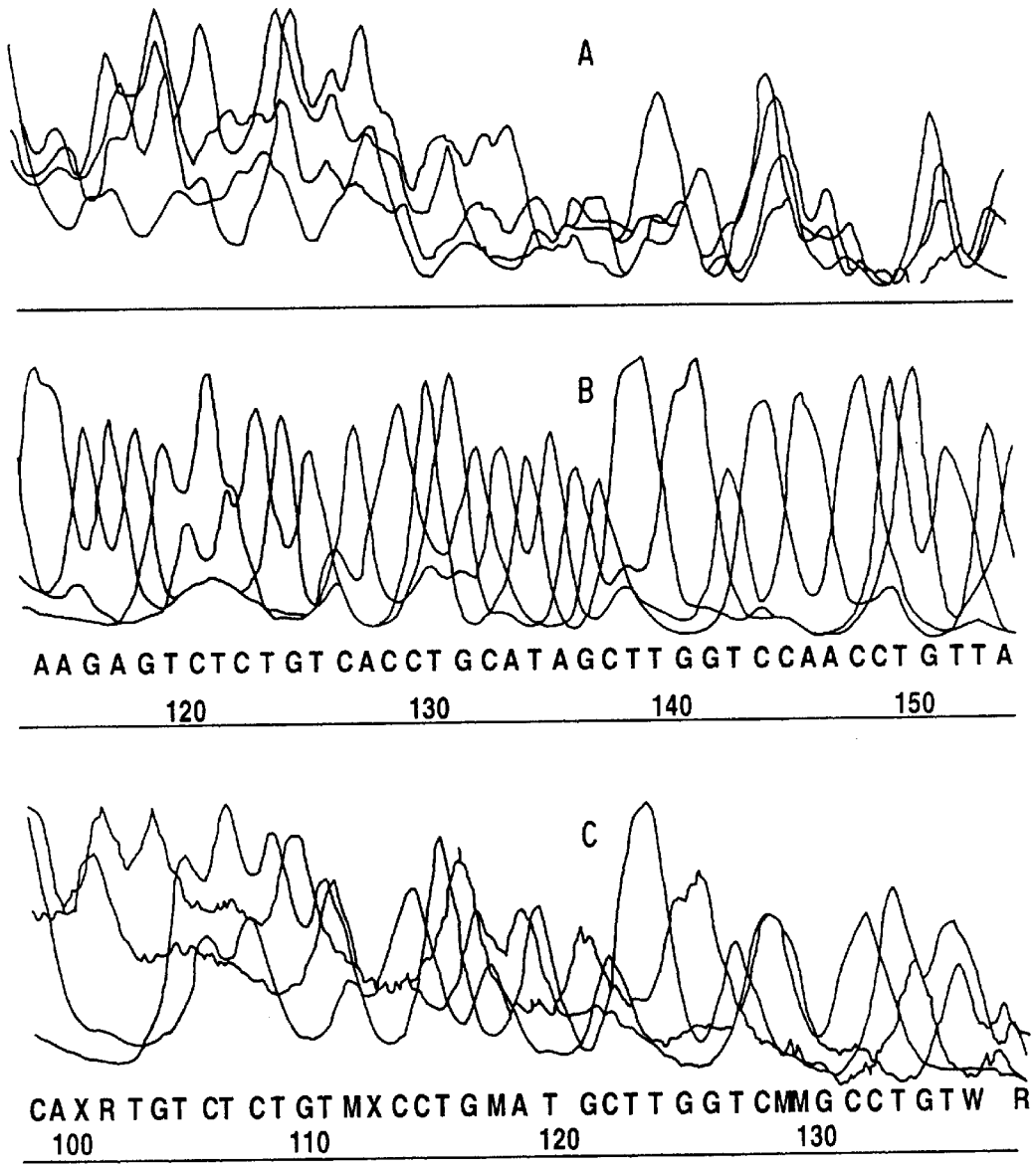
FIGS. 3A–3C. An uncoupled, direct, exponential amplification and sequencing reaction was carried out in combination with various thermostable polymerases which do not carry the "Tabor-Richardson" mutation.

Of the thermostable polymerases without a "Tabor-Richardson" mutation, a number of different polymerases were tested with regard to their effect on the direct, exponential amplification and sequencing reaction. Tth polymerase, Klentaq (U.S. Pat. No. 5, 436, 149, Korolev. S., et al., (1995) *Proc. Nati. Acad Sci. USA* 92, 9264–9268), Sequitherm® and standard Taq DNA polymerase were cycled with 60 ng total genomic DNA. Different unit amounts of 0.25 to 25 units (in the case of Klentaq) were tested for all polymerases (FIG. 3). The best results were achieved with Taq DNA polymerase.

EXAMPLE 5

Figure 4:
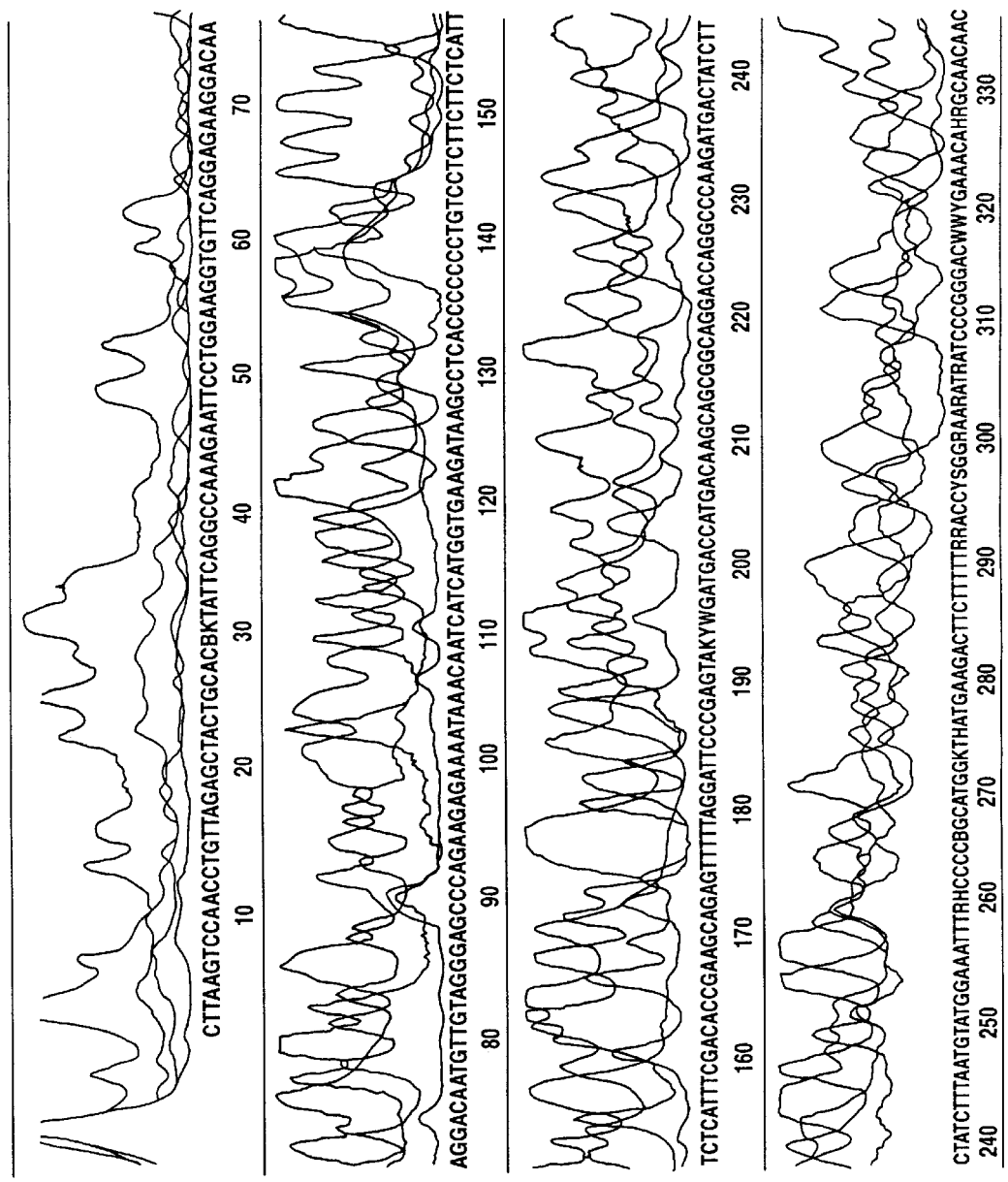
FIG. 4. 300 ng of total genomic human DNA was subjected to a direct, uncoupled, amplification and sequencing reaction using non-equimolar amount of primers i.e. 6 pmol of an FITC-labelled primer (CCR5-2) and 3 pmol of an unlabelled primer (CCR5-3). The primers span a region of 560 base pairs of the human single-copy gene CCR5. The A.L.F. software was able to process 260 bases. The reactions were carried out using 0.25 units Taq DNA polymerase and standard ThermoSequenase reagents.

In order to test whether DEXTAQ can be applied to single-copy DNA sequences if the primers are positioned at a distance of over 500 base pairs to one another, 300 ng total genomic human DNA was subjected to an uncoupled, direct, exponential amplification and sequencing reaction using non-equimolar amounts of an FITC-labelled and of an unlabelled primer (6 pmol:3 pmol) which span a region of 560 base pairs of the human single-copy gene. Good sequence curves were obtained for a length of about 300 base pairs (FIG. 4).

EXAMPLE 6

Figures 5, 5A:
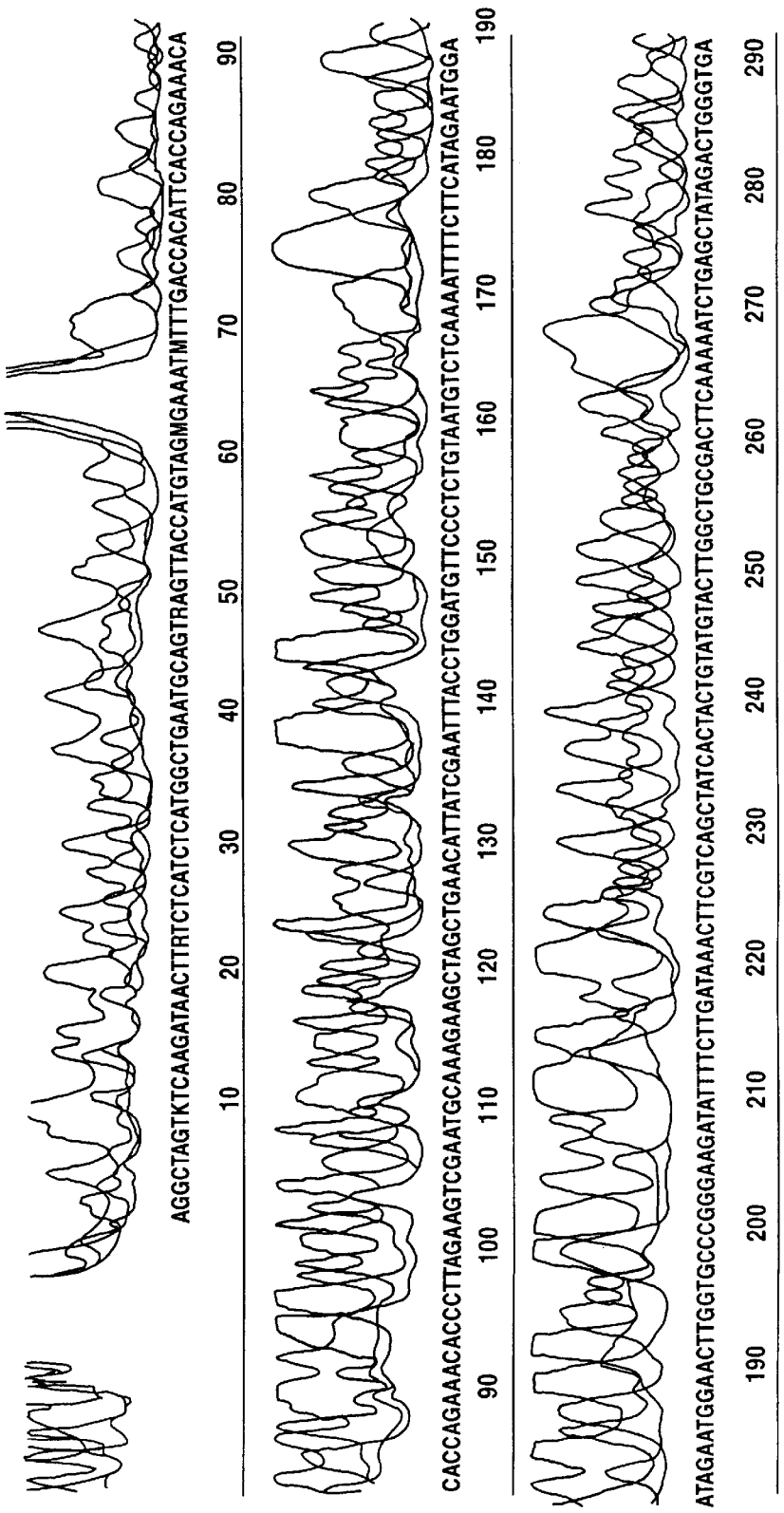
FIG. 5. 4 µl of a bacterial colony lysate was subjected to a direct, uncoupled amplification and sequencing reaction using non-equimolar amounts of differentially labelled primers i.e. 6 pmol of an FITC-labelled primer (universal) and 3 pmol of a Cy5-labelled primer (reverse). The primers span a region of 650 base pairs of the plasmid insert. The A.L.F. software was able to process 502 bases for the FITC labelled primer. The figure shows the curve results in the case of the FITC labelled universal primer. The reactions were carried out using 0.25 units Taq DNA polymerase and standard ThermoSequenase reagents.
Figure 5B:
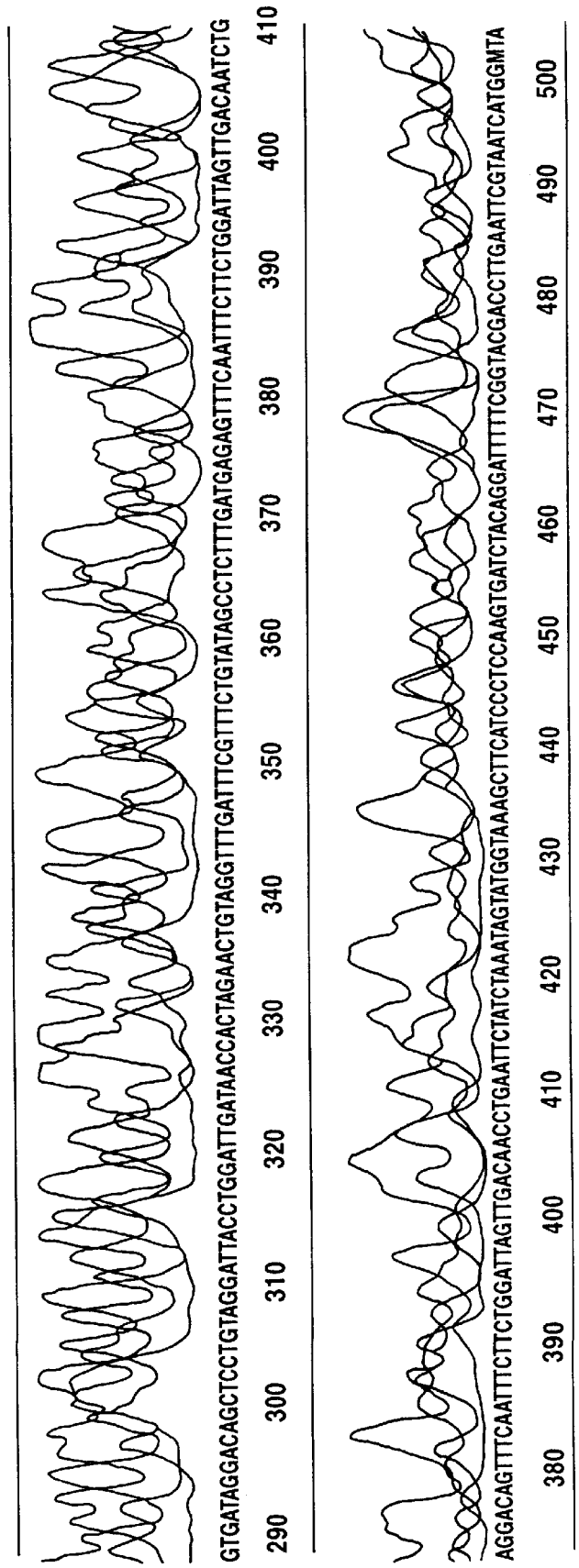

In order to test whether DEXTAQ can also be applied to plasmid sequencing of crude, bacterial lysates and in order to check whether DEXTAQ can be carried out using two differentially labelled primers, 4 µl of a bacterial colony lysate was subjected to an uncoupled ,direct, exponential amplification and sequencing reaction using non-equimolar amounts of differentially labelled primers i.e. 6 pmol of an FITC-labelled primer (universal) and 3 pmol of a Cy5-labelled primer (reverse). The primers span a length of 650 base pairs of the plasmid insert. The A.L.F. software was able in the case of the FITC-labelled primer to process 502 bases (FIG. 5).

What is claimed is:

1. A method for sequencing at least a portion of a nucleic acid molecule involving simultaneously amplifying the nucleic acid molecule and generating full length and truncated copies of the nucleic acid molecule for sequencing, comprising the steps of
   (a) subjecting a mixture in a single step to DNA amplification and generation of full length and truncated copies by subjecting the mixture to a thermocycling reaction, the thermocycling reaction comprises heat denaturation, annealing and synthesis, wherein said mixture comprises
       said nucleic acid molecule,
       a buffer solution,
       a first primer which is able to hybridize with a strand of said nucleic acid molecule,
       a second primer which is able to hybridize with a strand of said nucleic acid molecule complementary to the strand with which the first primer is able to hybridize, wherein at least one of the first and second primers is labelled,
       deoxynucleotides or deoxynucleotide derivatives, wherein said deoxynucleotide derivatives are able to be incorporated by a thermostable DNA polymerase into growing DNA molecules in place of one of dATP, dGTP, dTTP or dCTP,
       at least one dideoxynucleotide or another terminating nucleotide, and
       at least two thermostable DNA polymerases, wherein said at least two thermostable DNA polymerases are at least a first thermostable DNA polymerase and a second thermostable DNA polymerase, which second thermostable DNA polymerase has a reduced ability to incorporate said dideoxynucleotide or another terminating nucleotide compared with said first thermostable DNA polymerase, wherein a ratio of the amount, in unit, of said second thermostable DNA polymerase to the amount, in unit, of said first thermostable DNA polymerase is 1:X, wherein X is at least 16,
   to generate full-length and truncated copies of said nucleic acid molecule, wherein the full-length copies have a length equal to that of at least a portion of said nucleic acid molecule spanning the binding sites of the first and second primers;
   (b) making a sequence ladder using at least said truncated copies; and thereafter
   (c) reading the sequence ladder to obtain the sequence of said at least a portion of said nucleic acid molecule.

2. The method of claim 1, wherein the deoxynucleotide derivatives are thionucleotides, 7-deaza-2'-dGTP, 7-deaza-2'-dATP or deoxyinosine triphosphate.

3. The method of claim 1, wherein the thermocycling reaction is carried out from about 18 to about 50 cycles.

4. The method of claim 1, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

5. The method of claim 4, wherein said first thermostable DNA polymerase is a Taq DNA polymerase lacking 5'-3' exonuclease activity and having a Tabor-Richardson mutation.

6. The method of claim 5, wherein said first thermostable DNA polymerase is AmplitaqFS™, Taquenase™, or Thermo Sequenase™.

7. The method of claim 6, wherein said first thermostable DNA polymerase is Thermo Sequenase™.

8. The method of claim 1, wherein said second thermostable DNA polymerase is Taq DNA polymerase, Tth DNA polymerase, or Klentaq (Taq DNA polymerase)(-exo5'-3').

9. The method of claim 8, wherein said second thermostable DNA polymerase is Taq DNA polymerase.

10. The method of claim 7, wherein said first thermostable DNA polymerase is Thermo Sequenase™, and said second thermostable DNA polymerase is Taq DNA polymerase.

11. The method of claim 8, wherein said second thermostable DNA polymerase is Tth DNA polymerase, and wherein step (a) is carried out in the presence of $MnCl_2$ or Mn acetate.

12. The method of claim 1, wherein the thermocycling reaction in step (a) is carried out without interruption in a single container, vessel or tube.

13. The method of claim 1, wherein the ratio of said first primer to said second primer is not equal to 1:1.

14. The method of claim 13, wherein said ratio is between about 2:1 and about 3:1.

15. The method of claim 14, wherein said ratio is 2:1.

16. The method of claim 1, wherein the first and second primers are differently labelled.

17. The method of claim 1, wherein said annealing and synthesis of the thermocycling reaction is carried out at a temperature of at least 55° C.

18. The method of claim 1, wherein said nucleic acid molecule in said mixture is a human single-copy DNA.

19. The method of claim 1, wherein said mixture further comprises at least one thermostable pyrophosphatase.

20. The method of claim 1, wherein at least one of the first and second primers has a length that, in combination with a high annealing temperature, prevents annealing to unspecific DNA fragments during the heat denaturation of the thermocycling reaction.

21. The method of claim 20, wherein said length is at least 18 nucleotides.

22. The method of claim 1, wherein said nucleic acid molecule in said mixture is obtained from a body fluid, hairs, a cell, cells or fractions thereof, a tissue or fractions thereof, cell cultures or fractions thereof, bacteria or viruses.

23. The method of claim 1, wherein said nucleic acid molecule in said mixture is total genomic DNA.

24. The method of claim 23, wherein said total genomic DNA is unpurified.

25. The method of claim 1, wherein said nucleic acid molecule in said mixture is human genomic DNA.

26. The method of claim 1, wherein said nucleic acid molecule in said mixture is purified genomic DNA.

27. The method of claim 1, wherein said nucleic acid molecule in said mixture is unpurified plasmid DNA from bacteria.

28. The method of claim 23, wherein said total genomic DNA has a length of at least 2 kb.

29. The method of claim 1, wherein said nucleic acid molecule in said mixture comprises unpurified cloned DNA.

30. The method of claim 1, wherein said nucleic acid molecule in said mixture comprises purified cloned DNA.

31. The method of claim 1, wherein said nucleic acid molecule in said mixture is a single-copy DNA.

32. The method of claim 31, wherein said nucleic acid molecule in said mixture is at least about 60 ng of a single-copy DNA.

33. The method of claim 23, wherein said nucleic acid molecule in said mixture is at least about 60 ng of total genomic DNA.

34. The method of claim 1, wherein said annealing and synthesis of the thermocycling reaction is carried out at a temperature of at least 66° C.

35. The method of claim 1, wherein said annealing and synthesis of the thermocycling reaction is carried out at a temperature of at least 68° C.

36. The method of claim 1, wherein the molar ratio of said deoxynucleotides or deoxynucleotide derivatives to said at least one dideoxynucleotide or another terminating nucleotide is between 100:1 and 1000:1.

37. The method of claim 36, wherein the molar ratio of said deoxynucleotides or deoxynucleotide derivatives to said at least one dideoxynucleotide or another terminating nucleotide is between 300:1 and 600:1.

38. The method of claim 1, wherein said deoxynucleotides or deoxynucleotide derivatives are present at a concentration of about 300 μM to 2 mM.

39. The method of claim 1, wherein said at least one dideoxynucleotide or another terminating nucleotide is present at a concentration of about 1 to 5 μM.

40. The method of claim 1, wherein the length of the nucleic acid molecule in said mixture is at least 500 nucleotides between the 3' ends of the first and second primers.

41. The method of claim 4, wherein said nucleic acid molecule in said mixture comprises RNA and said second thermostable DNA polymerase has reverse transcriptase activity.

42. The method of claim 41, wherein said second thermostable DNA polymerase is Taq DNA polymerase.

43. The method of claim 41, wherein said second thermostable DNA polymerase is Tth DNA polymerase.

44. A kit for sequencing a nucleic acid molecule, comprising deoxynucleotides or deoxynucleotide derivatives, which deoxynucleotide derivatives are able to be incorporated by a thermostable DNA polymerase into growing DNA molecules in place of one of dATP, dGTP, dTTP or dCTP;

at least one dideoxynucleotide or another terminating nucleotide; and at least two thermostable DNA polymerases, wherein said at least two thermostable DNA polymerases are at least a first thermostable DNA polymerase and a second thermostable DNA polymerase, which second thermostable DNA polymerase has a reduced ability to incorporate said dideoxynucleotide or another terminating nucleotide in comparison to said first thermostable DNA polymerase, wherein a ratio of the amount, in unit, of said second thermostable DNA polymerase to the amount, in unit, of said first thermostable DNA polymerase is 1:X, wherein X is at least 16.

45. The kit of claim 44, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

46. The kit of claim 45, wherein said first thermostable DNA polymerase is a Taq DNA polymerase lacking 5'-3' exonuclease activity and having a Tabor-Richardson mutation.

47. The kit of claim 46, wherein said first thermostable DNA polymerase is AmplitaqFS™, Taquenase™, or ThermoSequenase™.

48. The kit of claim 47, wherein said first thermostable DNA polymerase is ThermoSequenase™.

49. The kit of claim 45, wherein said second thermostable DNA polymerase is Taq DNA polymerase, Tth DNA polymerase, or Klentaq (Taq DNA polymerase) (-exo5'-3').

50. The kit of claim 49, wherein said second thermostable DNA polymerase is Taq DNA polymerase.

51. The kit of claim 49, further comprising $MnCl_2$ or Mn acetate, wherein said second thermostable DNA polymerase is Tth DNA polymerase.

52. The kit of claim 45, further comprising a first primer which is able to hybridize with a strand of said nucleic acid molecule, and a second primer which is able to hybridize with a strand of said nucleic acid molecule complementary to the strand with which the first primer is able to hybridize, wherein the ratio of said first primer to said second primer is not equal to 1:1.

53. The kit of claim 52, wherein said ratio is between about 2:1 and about 3:1.

54. The kit of claim 53, wherein said ratio is 2:1.

55. The kit of claim 44, further comprising at least one thermostable pyrophosphatase.

56. The kit of claim 44, wherein said second thermostable DNA polymerase has reverse transcriptase activity.

57. The kit of claim 56, wherein said second thermostable DNA polymerase is Taq DNA polymerase.

58. The kit of claim 56, wherein said second thermostable DNA polymerase is Tth DNA polymerase.

59. The method of claim 1, wherein said ratio of the amount of the second thermostable DNA polymerase to the amount of the first thermostable DNA polymerase ranges from 1:320 to 1:16.

60. The method of claim 59, wherein said ratio of the amount of the second thermostable DNA polymerase to the amount of the first thermostable DNA polymerase ranges from 1:128 to 1:32.

61. The kit of claim 44, wherein said ratio of the amount of the second thermostable DNA polymerase to the amount of the first thermostable DNA polymerase ranges from 1:320 to 1:16.

62. The kit of claim 61, wherein said ratio of the amount of the second thermostable DNA polymerase to the amount of the first thermostable DNA polymerase ranges from 1:128 to 1:32.

* * * * *